(12) United States Patent
Phan

(10) Patent No.: US 6,939,350 B2
(45) Date of Patent: Sep. 6, 2005

(54) APPARATUS FOR SUPPORTING DIAGNOSTIC AND THERAPEUTIC ELEMENTS IN CONTACT WITH TISSUE INCLUDING ELECTRODE COOLING DEVICE

(75) Inventor: Huy D. Phan, San Jose, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 83 days.

(21) Appl. No.: 10/045,669

(22) Filed: Oct. 22, 2001

(65) Prior Publication Data

US 2003/0078644 A1 Apr. 24, 2003

(51) Int. Cl.⁷ .............................................. A61B 18/18
(52) U.S. Cl. ...................................................... 606/49
(58) Field of Search ........................ 606/27–52; 607/99

(56) References Cited

U.S. PATENT DOCUMENTS

| | | | |
|---|---|---|---|
| 4,326,529 A | 4/1982 | Doss et al. | |
| 5,085,657 A | 2/1992 | Ben-Simhon | |
| 5,281,213 A | * 1/1994 | Milder et al. | 606/15 |
| 5,292,320 A | 3/1994 | Brown et al. | |
| 5,330,518 A | * 7/1994 | Neilson et al. | 607/101 |
| 5,334,193 A | 8/1994 | Nardella | |
| 5,348,554 A | 9/1994 | Imran | |
| 5,383,876 A | 1/1995 | Nardella | |
| 5,409,483 A | 4/1995 | Campbell et al. | |
| 5,443,470 A | 8/1995 | Stern et al. | |
| 5,496,271 A | 3/1996 | Burton et al. | |
| 5,505,730 A | 4/1996 | Edwards | |
| 5,569,241 A | 10/1996 | Edwards | |
| 5,569,242 A | 10/1996 | Lax | |
| 5,584,872 A | 12/1996 | LaFontaine | |
| 5,609,151 A | 3/1997 | Mulier | |
| 5,624,392 A | 4/1997 | Saab | |
| 5,630,837 A | 5/1997 | Crowley | |
| 5,676,693 A | 10/1997 | LaFontaine | |
| 5,683,366 A | 11/1997 | Eggers | |
| 5,688,267 A | 11/1997 | Swanson et al. | |
| 5,697,536 A | 12/1997 | Eggers | |
| 5,697,882 A | 12/1997 | Eggers | |
| 5,697,927 A | 12/1997 | Imran et al. | |
| 5,785,706 A | 7/1998 | Bednarek | |
| 5,792,140 A | 8/1998 | Tu et al. | |
| 5,797,903 A | 8/1998 | Swanson et al. | |
| 5,800,482 A | 9/1998 | Pomeranz | |
| 5,800,484 A | 9/1998 | Gough | |
| 5,833,688 A | 11/1998 | Sieben et al. | |
| 5,879,347 A | 3/1999 | Saadat | |
| 5,879,348 A | 3/1999 | Owens | |
| 5,891,134 A | 4/1999 | Goble et al. | |
| 5,910,129 A | 6/1999 | Koblish | |
| 5,913,854 A | * 6/1999 | Maguire et al. | 606/41 |

(Continued)

FOREIGN PATENT DOCUMENTS

| | | |
|---|---|---|
| EP | 0856292 A1 | 8/1998 |
| EP | 1169972 A1 | 1/2002 |
| WO | WO-99/48421 A1 | 9/1999 |
| WO | WO-00/56237 A2 | 9/2000 |
| WO | WO 02/17804 A2 | 3/2002 |

OTHER PUBLICATIONS

PCT International Search Report dated Nov. 20, 2002 for PCT Application Serial No. PCT/US02/28088.
Claims as of Jan. 27, 2003, for U.S. Appl. No. 09/737,176.
Swanson et al., U.S. Appl. No. 09/652,099, filed Aug. 30, 2000.
Claims as of Oct. 6, 2002 for U.S. Appl. No. 09/652,099.

*Primary Examiner*—Michael Peffley
*Assistant Examiner*—Pete Vrettakos
(74) *Attorney, Agent, or Firm*—Henricks, Slavin & Holmes LLP

(57) ABSTRACT

Surgical methods and apparatus for coagulating tissue including an energy transmission device cooling apparatus.

50 Claims, 9 Drawing Sheets

U.S. PATENT DOCUMENTS

| | | |
|---|---|---|
| 5,938,659 A | 8/1999 | Tu et al. |
| 5,951,546 A | 9/1999 | Lorentzen |
| 5,957,922 A * | 9/1999 | Imran .......................... 606/41 |
| 5,961,490 A | 10/1999 | Adams |
| 5,961,513 A | 10/1999 | Swanson |
| 6,002,968 A | 12/1999 | Edwards |
| 6,012,457 A | 1/2000 | Lesh |
| 6,015,407 A | 1/2000 | Rieb et al. |
| 6,017,338 A | 1/2000 | Brucker et al. |
| 6,024,740 A | 2/2000 | Lesh |
| 6,032,077 A | 2/2000 | Pomeranz |
| 6,036,697 A | 3/2000 | DiCaprio |
| 6,048,329 A | 4/2000 | Thompson et al. |
| 6,053,912 A | 4/2000 | Panescu et al. |
| 6,053,937 A | 4/2000 | Edwards et al. |
| 6,068,653 A | 5/2000 | LaFontaine |
| 6,071,274 A | 6/2000 | Thompson |
| 6,071,279 A | 6/2000 | Whayne |
| 6,071,281 A | 6/2000 | Burnside |
| 6,076,012 A | 6/2000 | Swanson et al. |
| 6,117,101 A | 9/2000 | Diederich |
| 6,164,283 A | 12/2000 | Lesh |
| 6,168,594 B1 | 1/2001 | LaFontaine |
| 6,241,727 B1 | 6/2001 | Tu et al. |
| 6,258,087 B1 * | 7/2001 | Edwards et al. .............. 606/41 |
| 6,264,654 B1 * | 7/2001 | Swartz et al. ................. 606/45 |
| 6,270,493 B1 | 8/2001 | Lalonde et al. |
| 6,277,115 B1 | 8/2001 | Saadat |
| 6,280,441 B1 | 8/2001 | Ryan |
| 6,290,699 B1 | 9/2001 | Hall et al. |
| 6,306,133 B1 | 10/2001 | Tu et al. |
| 6,371,955 B1 | 4/2002 | Fuimaono |
| 6,485,489 B2 | 11/2002 | Teirstein et al. |
| 6,522,930 B1 * | 2/2003 | Schaer et al. .............. 607/101 |
| 6,579,288 B1 | 6/2003 | Swanson et al. |
| 6,837,885 B2 | 1/2005 | Koblish et al. |
| 2001/0007071 A1 | 7/2001 | Koblish et al. |
| 2002/0026187 A1 | 2/2002 | Swanson |
| 2002/0128640 A1 | 9/2002 | Swanson |
| 2003/0069570 A1 | 4/2003 | Witzel et al. |

* cited by examiner

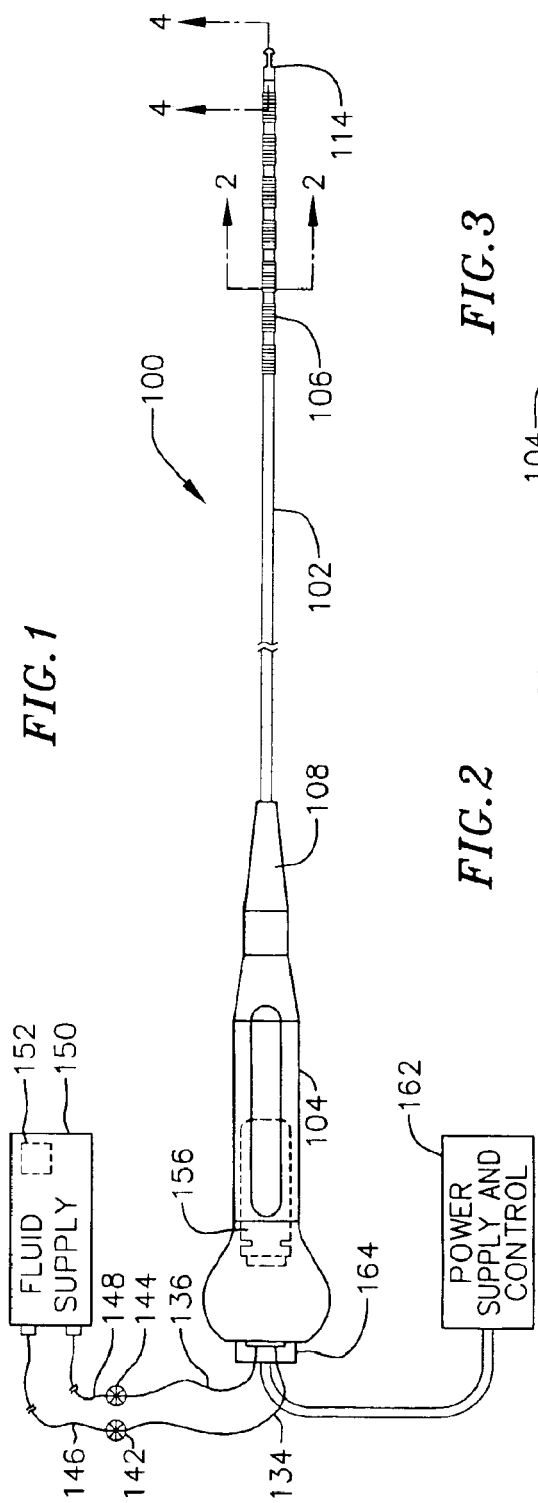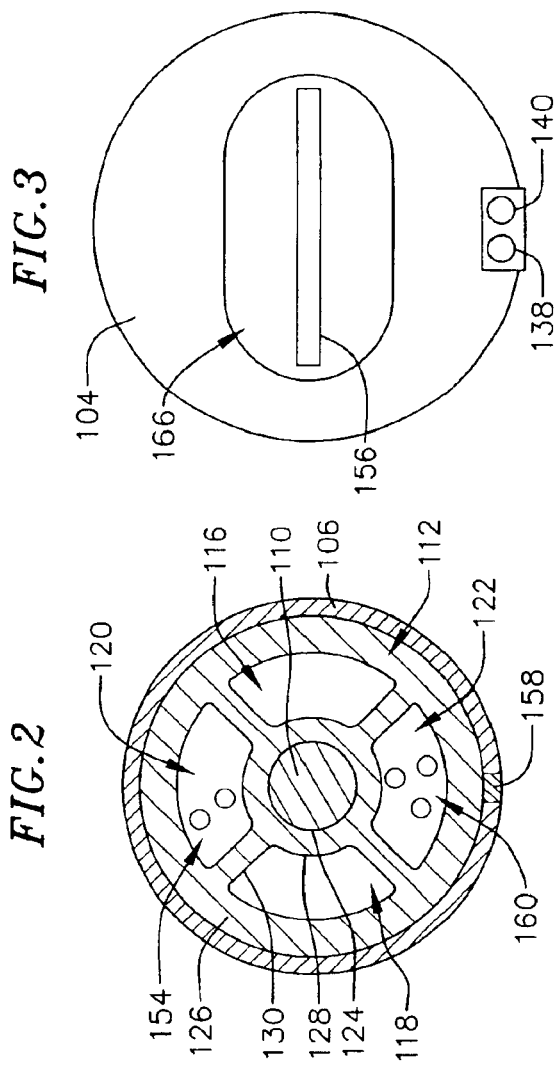

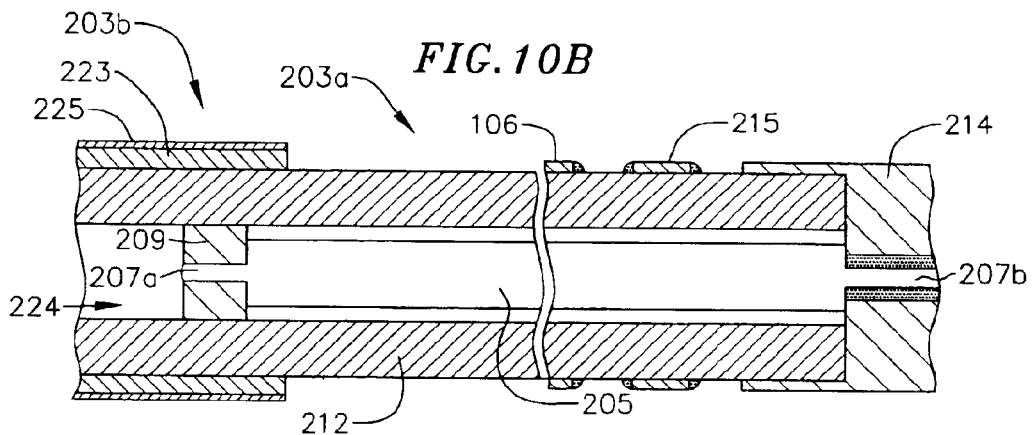
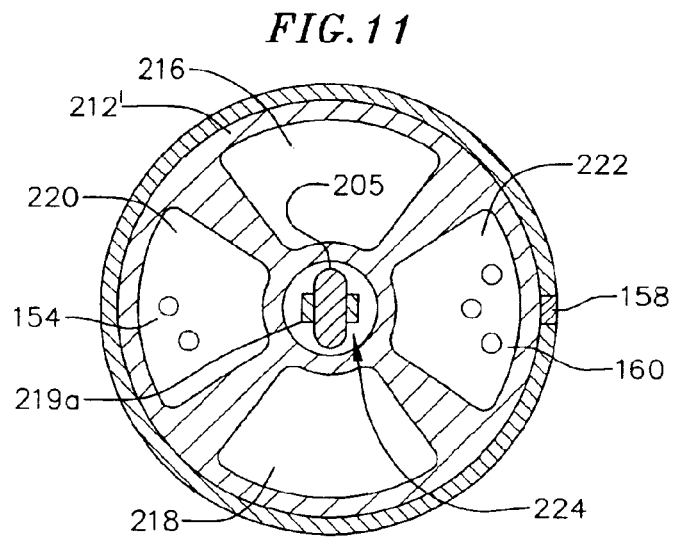
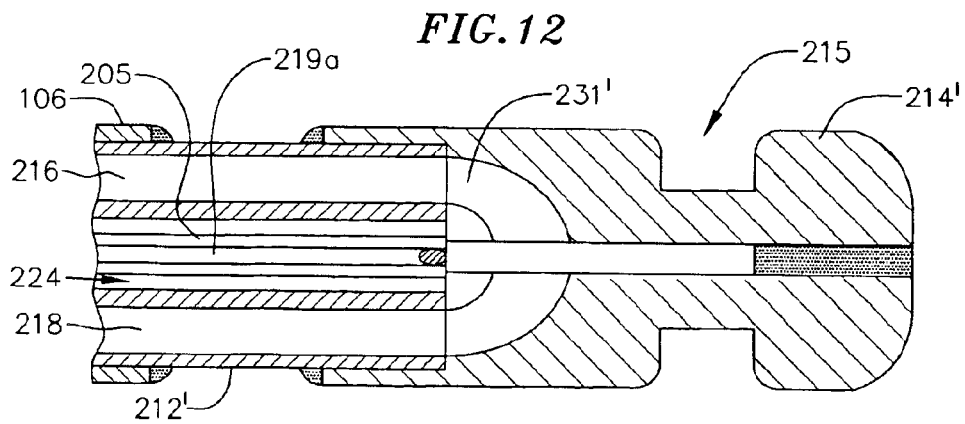

APPARATUS FOR SUPPORTING DIAGNOSTIC AND THERAPEUTIC ELEMENTS IN CONTACT WITH TISSUE INCLUDING ELECTRODE COOLING DEVICE

BACKGROUND OF THE INVENTIONS

1. Field of Inventions

The present inventions relate generally to structures for positioning diagnostic and therapeutic elements within the body and, more particularly, to devices which are particularly well suited for the treatment of cardiac conditions.

2. Description of the Related Art

There are many instances where diagnostic and therapeutic elements must be inserted into the body. One instance involves the treatment of cardiac conditions such as atrial fibrillation and atrial flutter which lead to an unpleasant, irregular heart beat, called arrhythmia.

Normal sinus rhythm of the heart begins with the sinoatrial node (or "SA node") generating an electrical impulse. The impulse usually propagates uniformly across the right and left atria and the atrial septum to the atrioventricular node (or "AV node"). This propagation causes the atria to contract in an organized way to transport blood from the atria to the ventricles, and to provide timed stimulation of the ventricles. The AV node regulates the propagation delay to the atrioventricular bundle (or "HIS" bundle). This coordination of the electrical activity of the heart causes atrial systole during ventricular diastole. This, in turn, improves the mechanical function of the heart. Atrial fibrillation occurs when anatomical obstacles in the heart disrupt the normally uniform propagation of electrical impulses in the atria. These anatomical obstacles (called "conduction blocks") can cause the electrical impulse to degenerate into several circular wavelets that circulate about the obstacles. These wavelets, called "reentry circuits," disrupt the normally uniform activation of the left and right atria.

Because of a loss of atrioventricular synchrony, the people who suffer from atrial fibrillation and flutter also suffer the consequences of impaired hemodynamics and loss of cardiac efficiency. They are also at greater risk of stroke and other thromboembolic complications because of loss of effective contraction and atrial stasis.

Although pharmacological treatment is available for atrial fibrillation and flutter, the treatment is far from perfect. For example, certain antiarrhythmic drugs, like quinidine and procainamide, can reduce both the incidence and the duration of atrial fibrillation episodes. Yet, these drugs often fail to maintain sinus rhythm in the patient. Cardioactive drugs, like digitalis, Beta blockers, and calcium channel blockers, can also be given to control the ventricular response. However, many people are intolerant to such drugs. Anticoagulant therapy also combats thromboembolic complications, but does not eliminate them. Unfortunately, pharmacological remedies often do not remedy the subjective symptoms associated with an irregular heartbeat. They also do not restore cardiac hemodynamics to normal and remove the risk of thromboembolism.

Many believe that the only way to really treat all three detrimental results of atrial fibrillation and flutter is to actively interrupt all of the potential pathways for atrial reentry circuits.

One surgical method of treating atrial fibrillation by interrupting pathways for reentry circuits is the so-called "maze procedure" which relies on a prescribed pattern of incisions to anatomically create a convoluted path, or maze, for electrical propagation within the left and right atria. The incisions direct the electrical impulse from the SA node along a specified route through all regions of both atria, causing uniform contraction required for normal atrial transport function. The incisions finally direct the impulse to the AV node to activate the ventricles, restoring normal atrioventricular synchrony. The incisions are also carefully placed to interrupt the conduction routes of the most common reentry circuits. The maze procedure has been found very effective in curing atrial fibrillation. However, the maze procedure is technically difficult to do. It also requires open heart surgery and is very expensive. Thus, despite its considerable clinical success, only a few maze procedures are done each year.

Maze-like procedures have also been developed utilizing catheters which can form lesions on the endocardium to effectively create a maze for electrical conduction in a predetermined path. Exemplary catheters are disclosed in U.S. Pat. Nos. 6,013,052, 6,203,525, 6,214,002 and 6,241,754. Typically, the lesions are formed by ablating tissue with an electrode carried by the catheter. Electromagnetic radio frequency ("RF") energy applied by the electrode heats, and eventually kills (i.e. "ablates"), the tissue to form a lesion. During the ablation of soft tissue (i.e. tissue other than blood, bone and connective tissue), tissue coagulation occurs and it is the coagulation that kills the tissue. Thus, references to the ablation of soft tissue are necessarily references to soft tissue coagulation. "Tissue coagulation" is the process of cross-linking proteins in tissue to cause the tissue to jell. In soft tissue, it is the fluid within the tissue cell membranes that jells to kill the cells, thereby killing the tissue.

Catheters used to create lesions (the lesions being 3 to 15 cm in length) typically include a relatively long and relatively flexible body portion that has one or more electrodes at or near its distal end. The portion of the catheter body portion that is inserted into the patient is typically from 23 to 55 inches in length and there may be another 8 to 15 inches, including a handle, outside the patient. The proximal end of the catheter body is connected to the handle which includes steering controls. The length and flexibility of the catheter body allow the catheter to be inserted into a main vein or artery (typically the femoral artery), directed into the interior of the heart, and then manipulated such that the electrode contacts the tissue that is to be ablated. Fluoroscopic imaging is used to provide the physician with a visual indication of the location of the catheter.

More recently, surgical soft tissue coagulation probes that carry one or more electrodes on relatively short, stiff shafts have been developed. Exemplary surgical probes are disclosed in U.S. Pat. No. 6,142,994. These probes may be used in endocardial and epicardial procedures where access to the heart is obtained by way of a thoracostomy, thoracotomy or median sternotomy. Such probes also allow endocardial lesions to be formed as a secondary procedure during a primary open heart surgical procedure such as mitral valve replacement, aortic valve replacement, and coronary artery bypass grafting.

Tissue temperature can be an issue in any lesion creation procedure. For example, a relatively wide deep lesion may be created by reducing the temperature of the tissue closest to the electrode. This shifts the hottest iso-thermal region deeper into the tissue, thereby enabling higher power to be delivered without causing char or excessive surface desiccation to occur. Higher power, in turn, results in a larger volume of tissue being heated to a temperature sufficient to coagulate tissue (above 50° C.) and, therefore, a wider and deeper lesion.

One method of reducing tissue temperature is to apply an electrically conductive cooling fluid to the tissue during a lesion formation procedure. The application of cooling fluid directly to tissue can, however, be problematic. It is very difficult to control the location of the cooling fluid on a beating heart because of the movement associated with beating and the curvature of the surface of the heart. It is also difficult to control the rate at which the fluid is delivered to the heart surface. The electrically conductive cooling fluid can, therefore, move to unintended areas. This makes it difficult to form the relatively narrow lesions that are preferred in epicardial and endocardial applications and leads to the coagulation of tissue other than the targeted tissue. The coagulation of non-targeted tissue is particularly problematic when lesions are being formed near nervous tissue such as the phrenic nerve.

Another method of reducing tissue temperature, which has been introduced in the catheter context, is the so-called "cooled tip" method. Here, a cooling medium is applied to the inner surface of a metallic tip electrode during a lesion formation procedure. Although the cooled tip method has proven to be an advance in the art, the use of tip electrodes is not always desirable. For example, elongate lesions must be formed by dragging a tip electrode along the tissue surface, which is slow and can result in gaps of conductive tissue that remain after the procedure is completed.

Accordingly, the inventor herein has determined that conventional methods of reducing tissue temperature are susceptible to improvement and, in particular, that a need exists for an apparatus including a cooled energy transmission device which is capable of forming an elongate lesion without being dragged or otherwise moved along the tissue surface.

SUMMARY OF THE INVENTIONS

A tissue coagulation device in accordance with a present invention includes a shaft, at least one energy transmission device, and an energy transmission device cooling apparatus. Such a device provides a number of advantages over the conventional lesion creation devices. The energy transmission device cooling capability, for example, allows the present device to form wider and deeper lesions than the conventional devices.

One particular implementation of the inventions includes an elongate energy transmission region formed by, for example, a plurality of spaced energy transmission devices. Each of the energy transmission devices is cooled by a cooling apparatus. Such a tissue coagulation device may be used to, for example, form an elongate lesion without moving the energy transmission devices. The present tissue coagulation device is, therefore, far less likely to leave the conductive gaps that sometimes remain when conventional cooled tip devices are dragged across tissue to form elongate lesions.

The above described and many other features and attendant advantages of the present inventions will become apparent as the inventions become better understood by reference to the following detailed description when considered in conjunction with the accompanying drawings.

BRIEF DESCRIPTION OF THE DRAWINGS

Detailed description of preferred embodiments of the inventions will be made with reference to the accompanying drawings.

FIG. 1 is a plan view showing a surgical probe in accordance with a preferred embodiment of a present invention.

FIG. 2 is a section view taken along line 2—2 in FIG. 1.

FIG. 3 is an end view of the exemplary surgical probe illustrated in FIG. 1.

FIG. 10b is a section view taken along line 10b—10b in FIG. 10a.

FIG. 11 is a section view in accordance with a preferred embodiment of a present invention.

FIG. 12 is a section view in accordance with a preferred embodiment of a present invention.

DETAILED DESCRIPTION OF THE PREFERRED EMBODIMENTS

Figure 4:
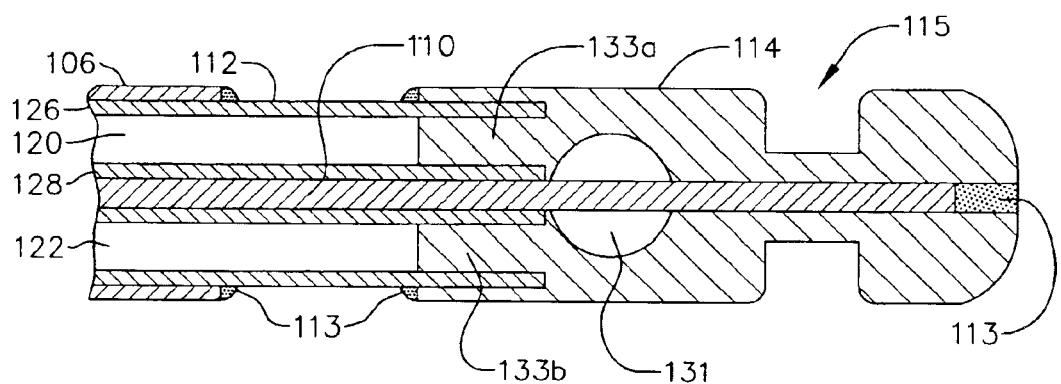
FIG. 4 is a section view taken along line 4—4 in FIG. 1.

The following is a detailed description of the best presently known modes of carrying out the inventions. This description is not to be taken in a limiting sense, but is made merely for the purpose of illustrating the general principles of the inventions.

The detailed description of the preferred embodiments is organized as follows:

I. Probe Structures
II. Electrode Cooling
III. Electrodes, Temperature Sensing And Power Control
IV. Exemplary Methods The section titles and overall organization of the present detailed description are for the purpose of convenience only and are not intended to limit the present inventions.

This specification discloses a number of structures, mainly in the context of cardiac ablation, because the structures are well suited for use with myocardial tissue. Nevertheless, it should be appreciated that the structures are applicable for use in therapies involving other types of soft tissue. For example, various aspects of the present inventions have applications in procedures concerning other regions of the body such as the prostate, liver, brain, gall bladder, uterus and other solid organs.

Additionally, although the illustrated embodiments are in the form of surgical probes, the present inventions also include catheter-based probes such as, for example, steerable catheters that support a plurality of longitudinally spaced electrodes near the distal end of the catheter body in addition to the cooling structures described below in the surgical probe context. Examples of such catheter based probes, to which the cooling structures described below may be added, include the catheters disclosed in aforementioned U.S. Pat. Nos. 6,013,052, 6,203,525, 6,214,002 and 6,241,754, which are incorporated herein by reference.

I. Probe Structures

As shown by way of example in FIGS. 1–5, a surgical probe 100 in accordance with a preferred embodiment of a present invention includes a relatively short shaft 102, a handle 104, and one or more electrodes 106 or other energy transmission devices on the distal portion of the shaft. [The electrodes 106 are discussed in greater detail in Section III below.] A strain relief element 108 may also be provided. The shaft 102 is preferably, although not necessarily, relatively stiff and about 5 inches to 20 inches in length, and most preferably about 8 inches to 12 inches in length. In the embodiment illustrated in FIGS. 1–5, the shaft 102 consists of a mandrel 110 and an electrically non-conductive outer structure 112 upon which the electrodes 106 are supported. The outer diameter of the outer structure 112 is preferably between about 5 French and about 12 French, but may vary to suit particular applications. The proximal end of the mandrel 110 is secured to the handle 104, while the distal end passes partially through, and is secured to, a tip member 114. The tip member 114 is, in turn, secured to the distal end of the outer structure 112 through the use of adhesive 113 or other suitable instrumentalities. The tip member 114 is preferably relatively soft at its distal end so as to prevent unintended tissue trauma and includes an indentation 115 that allows a suture to be attached thereto. A system for cooling the electrodes or other energy transmission devices is also provided, as is discussed in greater detail in Section II below.

The stiffness of the exemplary shaft 102, which as noted above is relatively stiff, is primarily a function of the mandrel 110 in the embodiment illustrated in FIGS. 1–5. As used herein the phrase "relatively stiff" means that the shaft (or other structural element) is either rigid, malleable, or somewhat flexible. A rigid shaft cannot be bent. A malleable shaft is a shaft that can be readily bent by the physician to a desired shape, without springing back when released, so that it will remain in that shape during the surgical procedure. Thus, the stiffness of a malleable shaft must be low enough to allow the shaft to be bent, but high enough to resist bending when the forces associated with a surgical procedure are applied to the shaft. A somewhat flexible shaft will bend and spring back when released. However, the force required to bend the shaft must be substantial.

One method of quantifying the flexibility of a shaft, be it shafts in accordance with the present inventions or the shafts of conventional catheters, is to look at the deflection of the shaft when one end is fixed in cantilever fashion and a force normal to the longitudinal axis of the shaft is applied somewhere between the ends. Such deflection ($\sigma$) is expressed as follows:

$$\sigma = WX^2(3L-X)/6EI$$

where:

W is the force applied normal to the longitudinal axis of the shaft,

L is the length of the shaft,

X is the distance between the fixed end of the shaft and the applied force,

E is the modulous of elasticity, and

I is the moment of inertia of the shaft.

When the force is applied to the free end of the shaft, deflection can be expressed as follows:

$$\sigma = WL^3/3EI$$

Assuming that W and L are equal when comparing different shafts, the respective E and I values will determine how much the shafts will bend. In other words, the stiffness of a shaft is a function of the product of E and I. This product is referred to herein as the "bending modulus." E is a property of the material that forms the shaft, while I is a function of shaft geometry. Therefore, a shaft formed from relatively soft material can have the same bending modulus as a shaft formed from relatively hard material, if the moment of inertia of the softer shaft is sufficiently greater than that of the harder shaft.

For example, a relatively stiff 2 inch shaft (either malleable or somewhat flexible) would have a bending modulus of at least approximately 1 lb.-in.$^2$ Preferably, a relatively stiff 2 inch shaft will have a bending modulus of between approximately 3 lb.-in.$^2$ and approximately 50 lb.-in.$^2$. By comparison, 2 inch piece of a conventional catheter shaft, which must be flexible enough to travel through veins, typically has bending modulus between approximately 0.1 lb.-in.$^2$ and approximately 0.3 lb.-in.$^2$. It should be noted that the bending modulus ranges discussed here are primarily associated with initial deflection. In other words, the bending modulus ranges are based on the amount of force, applied at and normal to the free end of the longitudinal axis of the cantilevered shaft, that is needed to produce 1 inch of deflection from an at rest (or no deflection) position.

As noted above, the deflection of a shaft depends on the composition and moment of inertia and, in the embodiment illustrated in FIGS. 1–5, primarily the composition and moment of inertia of the mandrel 110. The shaft could be made of elastic material, plastic material, elasto-plastic material, or a combination of materials as is the case in the exemplary shaft 102. By designing the shaft to be relatively stiff (and preferably malleable), the surgical tool is better adapted to the constraints encountered during the surgical procedure. The force required to bend a relatively stiff 2 inch long shaft should be in the range of approximately 1.5 lbs. to approximately 12 lbs. By comparison, the force required to bend a 2 inch piece of conventional catheter shaft should be between approximately 0.2 lb. to 0.25 lb. Again, such force values concern the amount of force, applied at and normal to the free end of the longitudinal axis of the cantilevered shaft, that is needed to produce 1 inch of deflection from an at rest (or no deflection) position.

Ductile materials are preferable in many applications because such materials can deform plastically before failure due to fracturing. Materials are classified as either ductile or brittle, based upon the percentage of elongation when the fracture occurs. A material with more than 5 percent elongation prior to fracture is generally considered ductile, while a material with less than 5 percent elongation prior to fracture is generally considered brittle. Material ductility can be based on a comparison of the cross sectional area at fracture relative to the original cross area. This characteristic is not dependent on the elastic properties of the material. Alternatively, the mandrel could be a mechanical component similar to shielded (metal spiral wind jacket) conduit or flexible Loc-Line®, which is a linear set of interlocking ball and socket linkages. These would be hinge-like segmented sections linearly assembled.

Rigid and somewhat flexible mandrels are preferably formed from stainless steel, while malleable mandrels are formed from annealed stainless steel or beryllium copper. In the exemplary embodiment illustrated in FIGS. 1–5, the mandrel 110 is a malleable rod that is about 0.03 inch in diameter. The outer structure 112 is flexible and has an outer diameter of about 5 French and about 12 French and an inner diameter that is about 0.002 inch larger than the diameter of the mandrel 110 for tolerance during assembly. As such, the shaft 102 as a whole is malleable. By selectively heat treating certain portions of the mandrel 110, some portions of the mandrel can be made more malleable than others if desired. Alternatively, the proximal portion of the mandrel 110 may be rigid and the distal portion malleable. Another alternative is to replace part of the distal portion of the mandrel 110 (e.g. the portion coextensive with the distal four of the electrodes 106) with a flexible spring member so that the distal portion of the shaft 102 includes both a malleable region and a flexible region. Such an arrangement is described in greater detail in U.S. application Ser. No. 09/536,095, which is entitled "Loop Structure For Positioning Diagnostic Or Therapeutic Element On The Epicardium Or Other Organ Surface" and incorporated herein by reference.

The outer structure 112 may be formed from any suitably electrically non-conductive and flexible material, such as electrically non-conductive plastics and ductile ceramic materials. As discussed in greater detail in Section II below, it is preferable that the material be relatively high in thermal conductivity and/or be relatively thin to promote heat transfer from the electrodes 106 to a cooling medium.

Another exemplary surgical probe is generally represented by reference numeral 200 and illustrated in FIGS. 8–10b. Surgical probe 200 is similar to surgical probe 100 and similar structural elements are represented by similar reference numerals. More specifically, surgical probe 200 includes a relatively short shaft 202, a handle 204, one or more electrodes 106 or other energy transmission devices, a strain relief element 208, an electrically non-conductive outer structure 212, and a tip member 214 with a relatively soft distal end and a suture indentation 215. The exemplary probe 200 also includes a cooling system for the energy transmission devices. [The cooling system and energy transmission devices are discussed in greater detail in Sections II and III below.] Here, however, the shaft 202 includes a steerable distal portion 203a, that is preferably about 2 inches to 6 inches in length and 5 French to about 10 French in diameter, and a proximal portion 203b, that is either rigid or malleable and preferably about 2 inches to 6 inches in length and about 5 French to about 16 French in diameter.

Figure 8:
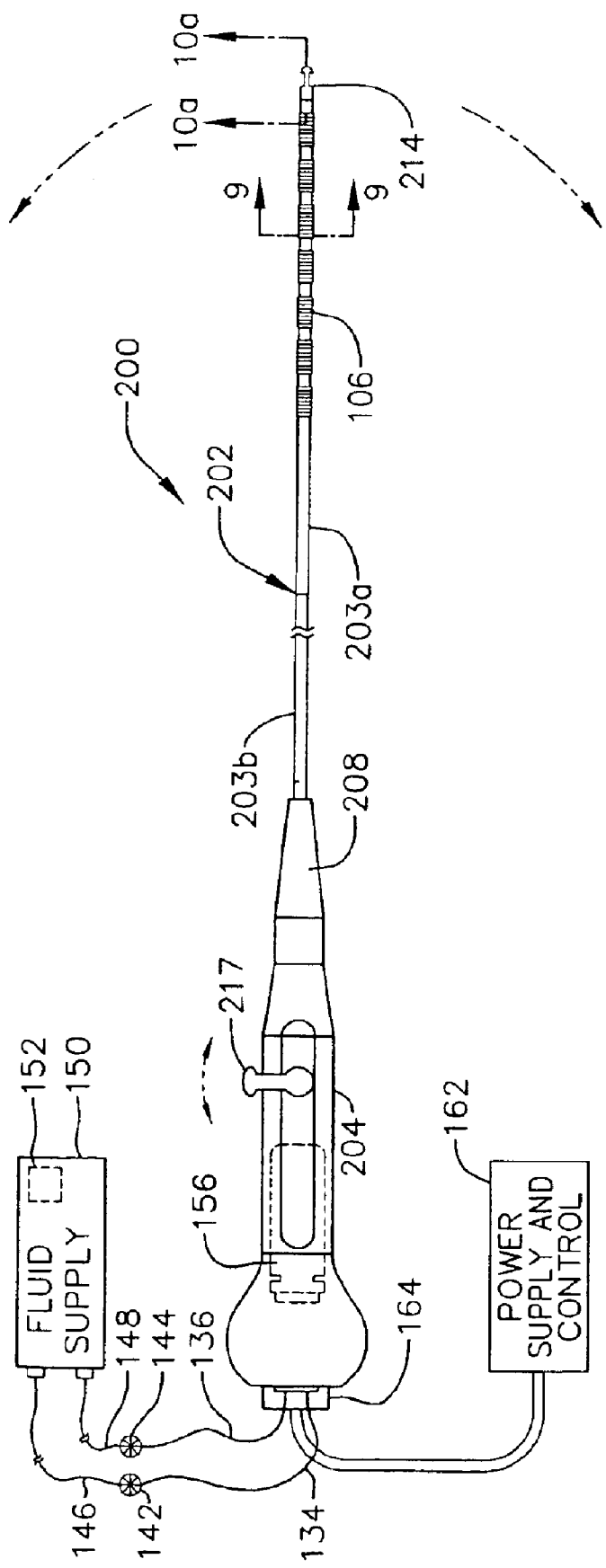
FIG. 8 is a plan view showing a surgical probe in accordance with a preferred embodiment of a present invention.
Figure 9:
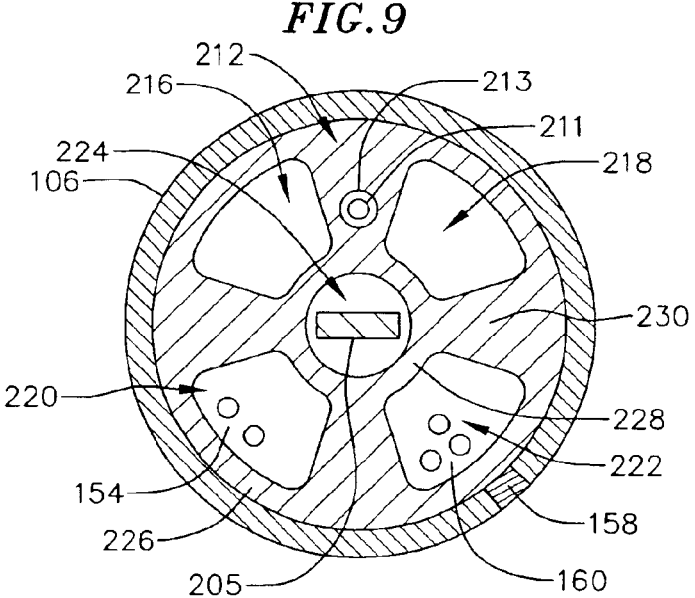
FIG. 9 is a section view taken along line 9—9 in FIG. 8.
Figure 10A:
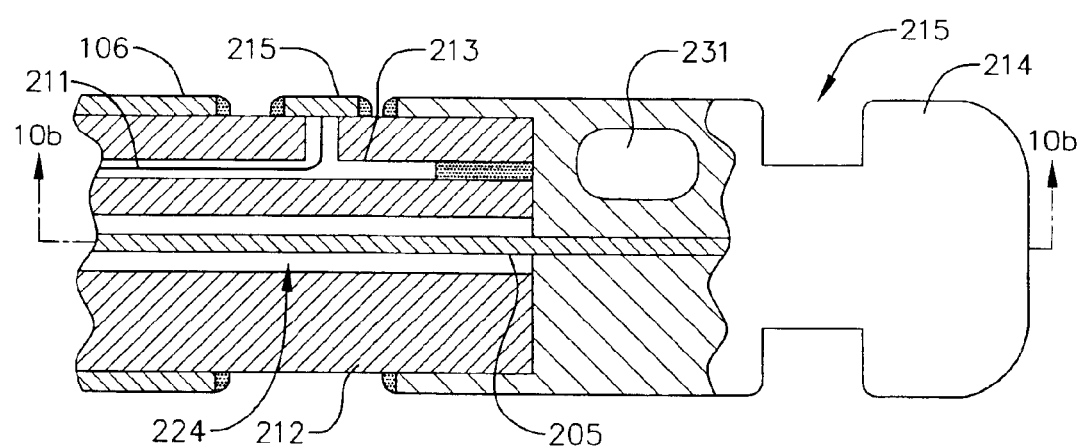
FIG. 10a is a section view taken along line 10a—10a in FIG. 9.

Referring more specifically to FIGS. 9–10b, the exemplary distal portion 203a is formed primarily by the flexible, electrically non-conductive outer structure 212, which supports the electrodes 106, and a steering center support 205 that is located within a lumen 224. The steering center support 205 is preferably about 0.05 inch wide, about 0.012 inch thick, about 2 inches to about 6 inches long, and formed from stainless steel. Of course, center supports formed from other materials and having different dimensions may also be used. In order to increase the stiffness of the center support 205, optional leaf springs (not shown) may also be provided on one or both sides of the center support. The center support 218 includes a pair of shoulders 207a and 207b. [FIG. 10b.] Shoulder 207a is inserted into a ferrule 209 that is mounted within the outer structure 212. Shoulder 207b is secured to the tip member 214 with solder or adhesive, while the tip member is itself bonded to the electrically non-conductive outer structure 212, thereby creating a rigid connection between the center support, tip member, and outer structure. The distal portion 203a in the exemplary probe 200 is deflected with a steering wire 211 that extends through a steering wire lumen 213 in the outer structure 212. [FIG. 9.] One end of the steering wire 211 is secured near the distal end of the outer structure 212 with an anchor 215, while the other end is secured to a control knob 217 on the handle 204. Rotation of the control knob 217 causes the distal section 203a to deflect in conventional fashion (note the arrows in FIG. 8).

It should be noted, however, that embodiments of the present inventions are not limited to any particular steering arrangement. For example, a second steering wire and steering wire lumen may be provided on the opposite side of the center support 205. Alternatively, as illustrated for example in FIGS. 11 and 12, a pair of steering wires 219a and 219b may be positioned within the lumen 224 of outer structure 212' and secured to the center support 205 with spot welds 221, solder, adhesive or other suitable instrumentalities.

The exemplary proximal portion 203b includes a relatively stiff hypotube 223, which is either rigid or malleable, and an outer polymer tubing 225 over the hypotube. [FIG. 10B.] In the illustrated embodiment, the outer structure 212 extends through the hypotube 223 to the handle so that the fluid inlet and outlet lumens 216 and 218 may be connected to infusion and ventilation lumens 134 and 136 (the lumens are discussed in Section II below). Alternatively, the non-conductive outer structure 212 may extend only a short distance into the distal end of the hypotube 223 and the infusion and ventilation lumens 134 and 136 extended through the hypotube to the inlet and outlet lumens 216 and 218.

Another exemplary surgical probe is generally represented by reference numeral 300 and illustrated in FIGS. 13–16. Surgical probe 300 is similar to surgical probe 200 and similar structural elements are represented by similar reference numerals. More specifically, the surgical probe 300 includes a relatively short shaft 302 with a distal portion 303a and a proximal portion 303b, a handle 304, one or more electrodes 306 or other energy transmission devices, a strain relief element 308, and a tip member 314. The exemplary probe 300 also includes a cooling system for the energy transmission devices. [The cooling system and energy transmission devices are discussed in greater detail in Sections II and III below.] However, instead of having a steerable distal portion, the distal portion 303a is pre-shaped for particular functions or procedures. Although not so limited, the illustrated distal portion 303a is semi-circular (i.e. defines an arc of about 180 degrees) and is in-plane with the proximal portion 303b. This shape is particularly useful for positioning the distal portion 303a around anatomical structures such as pulmonary veins. Other pre-shaped curvatures include, but are not limited to, those that range from a few degrees to a complete circle, those which result in some or all of the distal portion 303a being in a different plane than the proximal portion 303b, or in multiple planes as would be the case with a helical distal portion.

The exemplary distal portion 303a consists primarily of an electrically non-conductive outer structure 312 that is preferably about 2 inches to 6 inches in length and 5 French to about 10 French in diameter. The proximal portion 303a, which is preferably either rigid or malleable and preferably about 2 inches to 6 inches in length and about 5 French to about 16 French in diameter, consists of a consists of a relatively stiff hypotube and an outer polymer tubing over the hypotube similar to that described above with reference to FIG. 10B. Here too, the outer structure 312 extends through the hypotube to the handle so that the fluid inlet and outlet lumens 316 and 318 may be connected to infusion and ventilation lumens 134 and 136 (the lumens are discussed in Section II below). Alternatively, the non-conductive outer structure 312 may extend only a short distance into the distal end of the hypotube and the infusion and ventilation lumens 134 and 136 extended through the hypotube to the inlet and outlet lumens 316 and 318.

II. Electrode Cooling

The electrode cooling apparatus disclosed herein employ fluid to cool the electrodes (or other energy transmission devices) during coagulation procedures. Although gaseous cooling fluid may be employed, liquid is preferred. As described in greater detail below, heat from the electrodes is transferred to the fluid to cool the electrodes while energy is transferred from the electrodes to the tissue. Cooling the electrodes during a coagulation procedure facilitates the formation of lesions that are wider and deeper than those that could be realized with an otherwise identical device which lacks the present cooling apparatus.

Turning first to the preferred embodiments illustrated in FIGS. 1–7, the electrode cooling apparatus is composed primarily of the electrically non-conductive outer structure 112, which supports the electrodes 106, and the fluid inlet and outlet lumens 116 and 118 formed therein. Heat from the electrodes 106 is transferred through the outer structure 112 to fluid that is flowing through the inlet and outlet lumens 116 and 118. Accordingly, in addition to being electrically non-conductive, the material used to form the outer structure 112 should be relatively high in thermal conductivity. As used herein, "relatively high" thermal conductivity is at least about 0.8 W/m·K and preferably ranges from about 0.8 to about 30 (or more) W/m·K. Suitable electrically non-conductive, thermally conductive thermoplastics for the outer structure 112 in a probe with a relatively stiff electrode supporting portion, such as the exemplary probe 100, include RTP 0299×85175 D nylon manufactured by RTP Company in Winona, Minn. and CoolPoly™ RS007 polyphenylene sulfide and RS008 nylon manufactured by Cool Polymers, Inc. in Warwick, R.I.

Figure 5:
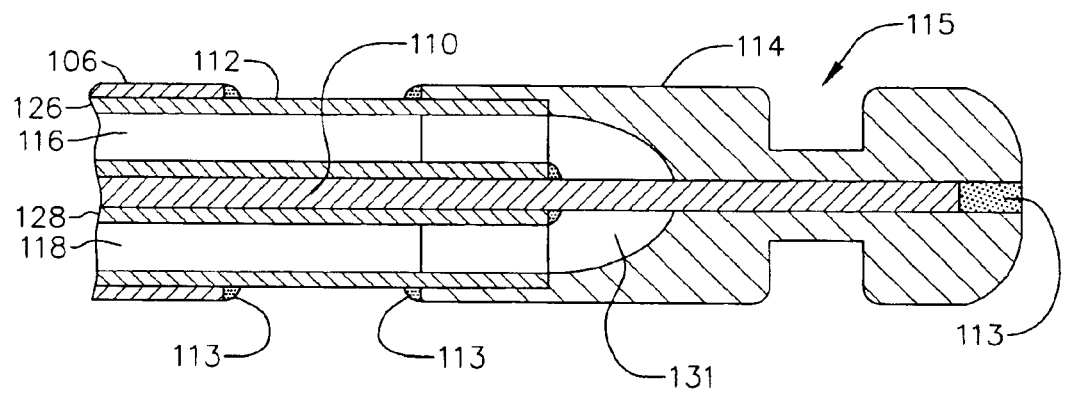
FIG. 5 is a section view taken along line 4—4 in FIG. 1 and rotated 90 degrees relative to the view illustrated in FIG. 4.

Heat transfer may also be promoted by minimizing the thickness of the electrically non-conductive material between the fluid lumens and the energy transmission devices and by maximizing the cross-sectional area of the fluid lumens. Referring to FIGS. 2, 4 and 5, the exemplary outer structure 112 is a multi-lumen structure which includes the aforementioned fluid inlet and outlet lumens 116 and 118, a power wire lumen 120, a signal wire lumen 122 (the power wires 154 and signal wires 160 are discussed in Section III below), and a central lumen 124 through which the mandrel 110 extends. The lumen arrangement divides the outer structure 112 into an outer wall 126, an inner wall 128 and a plurality of side walls 130 extending therebetween. Preferably, in an implementation where the outer diameter of the outer structure 112 is about 8 French (0.105 inch), the thickness of the outer wall 126 will be about 0.003 inch to about 0.014 inch. It should be noted that when the outer wall thickness is about 0.010 inch or less, materials with less than "relatively high" thermal conductivities, such as Pebax® material and polyurethane, may also be used.

In order to allow the fluid inlet and outlet lumens 116 and 118 to occupy as much of the cross-sectional area and circumferential area of the outer structure 112 as possible, the power and signal wire lumens 120 and 122 should be just large enough to accommodate the power and signal wires 154 and 160. The width of the fluid lumens 116 and 118 (i.e. the distance between the outer wall 126 and inner wall 128) should be at least 2 times the thickness of outer wall 126 and, preferably 4 times the thickness of the outer wall. In an implementation where the outer diameter of the outer structure 112 is about 8 French (0.105 inch), and the thickness of the outer wall 126 is about 0.004 inch to about 0.010 inch, the width of the fluid lumens 116 and 118 is preferably about 0.020 inch to about 0.040 inch.

The inlet lumen 116 may connected to the outlet lumen 118 by a connection lumen 131 formed in the exemplary tip member 114. [FIGS. 4 and 5.] The mandrel 100 passes through the connection lumen 131 and the cooling fluid flows around the mandrel. Such a tip member may be formed from, for example, two molded electrically non-conductive plastic parts. The exemplary tip member 114 also includes a pair of plugs 133a and 133b to seal the power and signal wire lumens 120 and 122.

Figure 6:
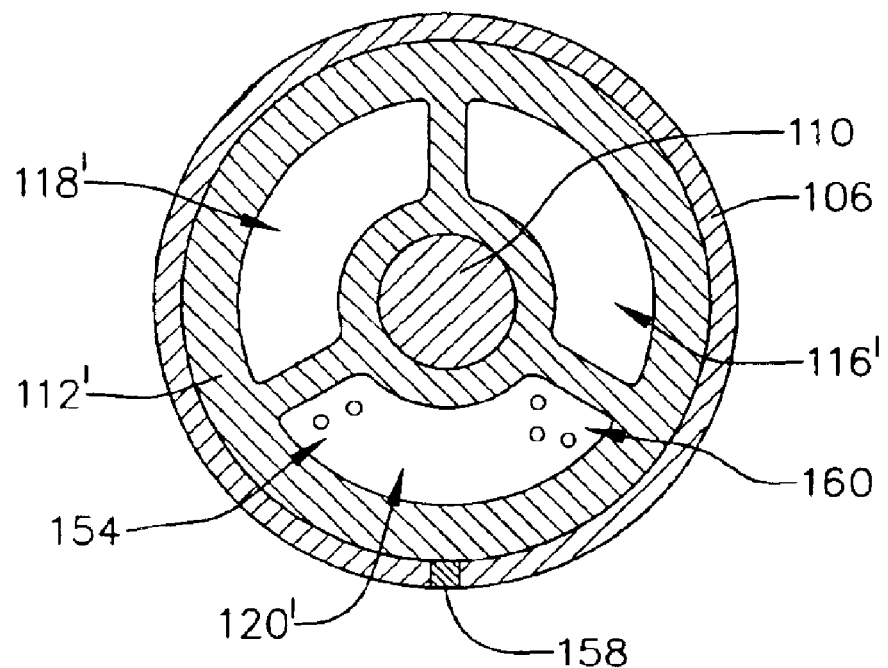
FIG. 6 is a section view in accordance with a preferred embodiment of a present invention.

As illustrated for example in FIG. 6, an alternative exemplary outer structure 112' includes a single wire lumen 120' for power and signal wires in addition to the inlet and outlet lumens 116' and 118'. Here, the tip member lumen 131 would have to be slightly reconfigured and one of the plugs 133a/133b eliminated. The wire lumens may also be eliminated altogether in those instances where the power and signal wires are sufficiently insulated and/or the cooling fluid is sufficiently non-conductive. Another alternative configuration is to arrange the lumens such that the power and signal wire lumens 120 and 122 are next to each other. Still another alternative configuration is a central inlet (or outlet) lumen that is connected to an outlet (or inlet) lumen that extends all, or essentially all, of the way around the outer structure. A similar configuration, albeit without a non-conductive outer structure, is discussed in Section IV below with reference to FIG. 17.

Figure 7:
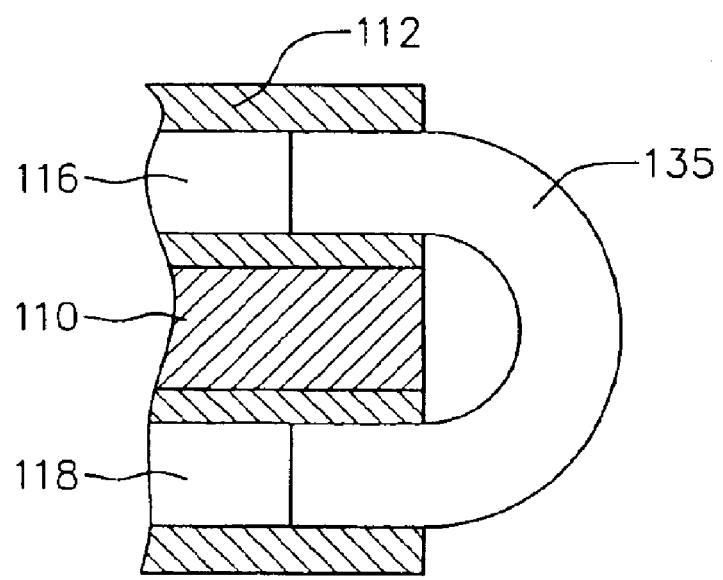
FIG. 7 is a side, partial section view in accordance with a preferred embodiment of a present invention.

As illustrated for example in FIG. 7, the tip member 114 may be replaced by a flexible tube 135 that connects the fluid inlet and outlet lumens 116 and 118. A pair of plugs (not shown) would be provided for the power and signal wire lumens 120 and 122 when the flexible tube 132 is employed. A similar flexible tube may also be employed in the embodiments illustrated in FIGS. 8–16.

Fluid may be supplied to the surgical probe 100 by way of an infusion lumen 134, which is connected to the inlet lumen 116, and exit by way of a ventilation lumen 136, which is connected to the outlet lumen 118, as is illustrated for example in FIG. 1. The infusion and ventilation lumens 134 and 136 extend through a pair of apertures 138 and 140 in the handle 104. [FIG. 3.] The proximal ends of the infusion and ventilation lumens 134 and 136 are provided with on-off valves 142 and 144, which may be connected to the infusion and ventilation lines 146 and 148 of a fluid supply device 150 with a control system 152 such as, for example, an infusion pump capable of variable flow rates.

With respect to fluid temperature and flow rate, a suitable inlet temperature is about 0 to 25° C. and the fluid supply device 150 may be provided with a suitable cooling system, if desired, to bring the temperature of the fluid down to the desired level. Although the fluid temperature will rise as heat is transferred to the fluid, the temperature will remain low enough to draw heat from the energy transmission devices as it flows through the inlet and outlet lumens 116 and 118. In a seven electrode embodiment such as those illustrated in FIGS. 1–7 where 150 W is being supplied to the electrodes 106, for example, a suitable constant fluid flow rate is about 5 ml/min to about 20 ml/min. In a closed system such as that illustrated in FIG. 1 where the fluid is stored in the fluid supply device 150 and heated fluid is returned to the device, it has been found that a volume of fluid between about 10 and about 60 ml within the device will remain at room temperature (about 22° C.) when the flow rate is between about 5 ml/min. and about 20 ml/min. Alternatively, in an open system where heated fluid is not returned to the fluid supply device 150, the device should include enough fluid to complete the procedure. 60 ml would, for example, be required for a 3 minute procedure where the flow rate was 20 ml/min.

The cooling fluid itself is not limited to any particular fluid. Preferably, however, the fluid will be a low or non-conductive fluid such as sterile water or 0.9% saline solution.

Electrode cooling in the exemplary embodiments illustrated in FIGS. 8–16 is accomplished in essentially the same way that it is in the exemplary embodiments described above with respect to FIGS. 1–7. Referring first to the exemplary probe 200 illustrated in FIGS. 8–10b, the electrode cooling apparatus is composed primarily of the electrically nonconductive outer structure 212, which supports the electrodes 106, and the fluid inlet and outlet lumens 216 and 218 that are formed therein. As such, the outer structure 212 should be formed from electrically non-conductive materials with relatively high thermal conductivity. The inlet and outlet lumens 216 and 218 are connected to one another by way of a connector lumen 231 (FIG. 10a) formed in the tip member 214. The inlet and outlet lumens 216 and 218 may also be connected to, for example, the fluid source 150 by way of the infusion and ventilation lumens 134 and 136 in the manner described above.

The exemplary outer structure 212 also includes a power wire lumen 220, a signal wire lumen 222 (the power wires 154 and signal wires 160 are discussed in Section III below), and a central lumen 224 for the steering center support 205. Here too, the lumen arrangement divides the outer structure 212 into an outer wall 226, an inner wall 228 and a plurality of side walls 230 extending therebetween. Preferably, in an implementation where the outer diameter of the outer structure 212 is about 8 French (0.105 inch), the thickness of the outer wall 226 will be about 0.003 inch to about 0.014 inch. It should be noted that when the outer wall thickness is about 0.010 inch or less, materials with less than "relatively high" thermal conductivities may be used.

In order to allow the fluid inlet and outlet lumens 216 and 218 to occupy as much of the cross-sectional area and circumferential area of the outer structure 212 as possible, the power and signal wire lumens 220 and 222 should be just large enough to accommodate the power and signal wires 154 and 160. The width of the fluid lumens 216 and 218 (i.e. the distance between the outer wall 226 and inner wall 228) should be at least 2 times the thickness of outer wall 226 and, preferably 4 times the thickness of the outer wall. In an implementation where the outer diameter of the outer structure 212 is about 8 French (0.105 inch), and the thickness of the outer wall 226 is about 0.004 inch to about 0.010 inch, the width of the fluid lumens 216 and 218 is preferably about 0.020 inch to about 0.040 inch.

With respect to materials, the steerable distal portion 203a illustrated in FIGS. 8–12 requires greater flexibility than the relatively stiff shaft 102 illustrated in FIGS. 1–7. Accordingly, the outer structure 212 is preferably formed with flexible thermoplastic polymer materials, such as nylon or polyurethane, which are filled with a filler that promotes heat transfer. Suitable fillers include graphite, aluminum, tungsten and ceramic powders. Another suitable filler is Carborundum CarboTherm™ boron nitride powder manufactured by Saint-Gobain in Cavaillon, France. Such fillers may also be added to the materials used to form the outer structures 112 and 312 employed in exemplary probes 100 and 300 to improve heat transfer.

Turning to FIGS. 11 and 12, in which an alternate steering arrangement is illustrated, the outer structure 212' is substantially identical to the outer structure 212 in that it includes fluid inlet and outlet lumens 216 and 218 as well as power and signal wire lumens 220 and 222. Here, however, the inlet and outlet lumens are located on opposite sides of the central lumen 224. The tip member 214' and connector lumen 231' are reconfigured accordingly, as compared to the tip member 214 and connector lumen 231, to accommodate the modified outer structure 212'.

The electrode cooling apparatus in the exemplary probe 300 illustrated in FIGS. 13–16 is also composed primarily of the electrically non-conductive outer structure 312, which supports the electrodes 306, and the fluid inlet and outlet lumens 316 and 318 that are formed therein. As such, the outer structure 312 should be formed from electrically non-conductive materials with relatively high thermal conductivity. The inlet and outlet lumens 316 and 318 are connected to one another by way of a connector lumen 331 (FIG. 15) formed in the tip member 314. The inlet and outlet lumens 316 and 318 may also be connected to, for example, the fluid source 150 by way of the infusion and ventilation lumens 134 and 136 in the manner described above.

Figure 14:
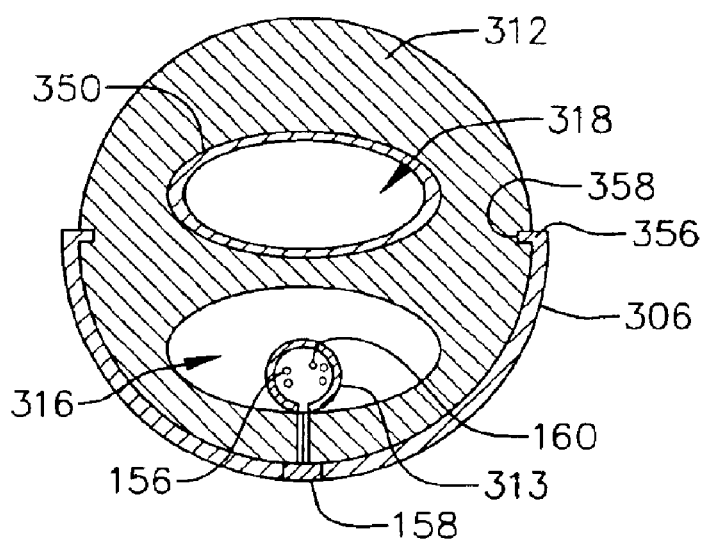
FIG. 14 is a section view taken along line 14—14 in FIG. 13.
Figure 15:
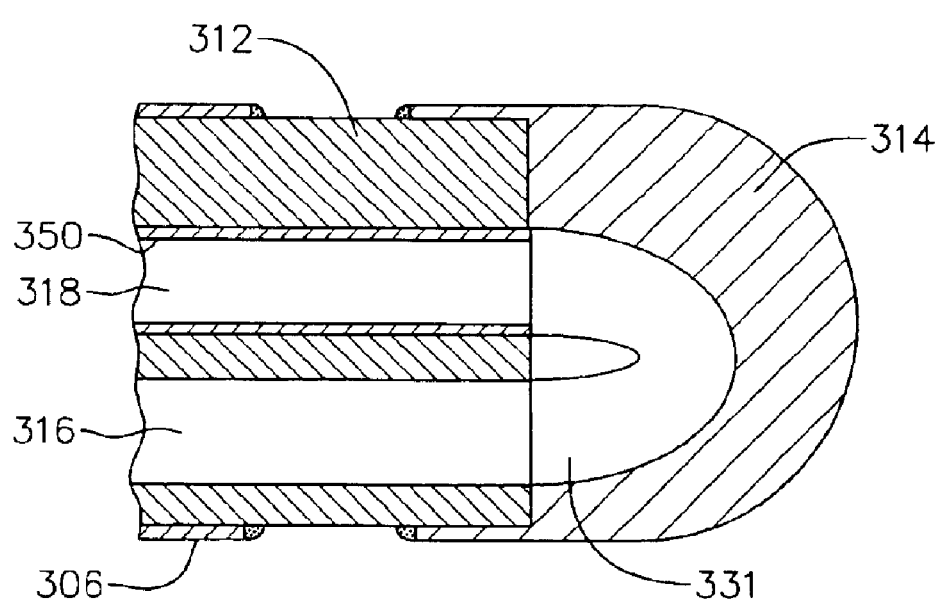
FIG. 15 is a section view taken along line 15—15 in FIG. 13.

In contrast to the previously described embodiments, there are no separate power and signal wire lumens. Instead, the power and signal wires 156 and 160 may either be located within a tubular member 313 that is itself located within the inlet lumen 316 as illustrated in FIG. 14, or simply be placed within the inlet lumen with sufficient insulation. Additionally, although any of the energy transmission devices described in Section III below may be used in the exemplary probe 300, the exemplary electrodes 306 extend only partially around the outer structure 312. To optimize heat transfer when this type of electrode is employed, it is preferable that the inlet lumen 316 be positioned adjacent to the electrodes 306 and that the outlet lumen 318 be provide with a layer of thermal insulation 350 to prevent the transfer of heat from the heated fluid within the outlet lumen to the outer structure 312, as is illustrated for example in FIG. 14. The insulation should be removed when an electrode extends all the way around the outer structure 312. Similar positioning and insulation would also be employed in those instances where the electrodes 306 are used in conjunction with the exemplary probes illustrated in FIGS. 1–12. Preferably, the thickness of the wall between the electrodes 306 and the fluid inlet lumen 316 will be about 0.001 inch to about 0.020 inch to promote heat transfer.

With respect to materials, the distal portion 303a should be formed from materials that will maintain the desired distal portion shape (typically created during an injection molding process), as well as provide the desired electrical insulation and heat transfer properties. The aforementioned RTP 0299x85175 nylon is a suitable material for this purpose. Thermally conductive liquid crystal polymers, such as CoolPoly™ D2 and E200, which is manufactured by Cool Polymers, Inc., Vectra®, which is manufactured by Ticona in Summit, N.J., and Xydar®, which is manufactured by BP Amoco Chemicals in Alpharetta, Ga. may also be employed. Ductile ceramic materials are also suitable.

III. Electrodes, Temperature Sensing and Power Control

In each of the illustrated embodiments, a plurality of spaced electrodes adapted to transmit RF energy are employed. However, devices such as ultrasonic transducers and microwave electrodes may be substituted for the electrodes.

The exemplary probe 100 illustrated in FIGS. 1–7 includes seven spaced electrodes 106. The spaced electrodes 106 are preferably in the form of wound, spiral closed coils. The coils are made of electrically conducting material, like copper alloy, platinum, or stainless steel, or compositions such as drawn-filled tubing (e.g. a copper core with a platinum jacket). The electrically conducting material of the coils can be further coated with platinum-iridium or gold to improve its conduction properties and biocompatibility. Preferred coil electrodes is disclosed in U.S. Pat. Nos. 5,797, 905 and 6,245,068.

Alternatively, the electrodes may be in the form of solid rings of conductive material, like platinum, or can comprise a conductive material, like platinum-iridium or gold, coated upon the device using conventional coating techniques or an ion beam assisted deposition (IBAD) process. For better adherence, an undercoating of nickel, silver or titanium can be applied. The electrodes can also be in the form of helical ribbons. The electrodes can also be formed with a conductive ink compound that is pad printed onto a non-conductive tubular body. A preferred conductive ink compound is a silver-based flexible adhesive conductive ink (polyurethane binder), however other metal-based adhesive conductive inks such as platinum-based, gold-based, copper-based, etc., may also be used to form electrodes. Such inks are more flexible than epoxy-based inks. Open coil electrodes may also be employed.

The portion of the electrodes 106 that are not intended to contact tissue (and be exposed to the blood pool) may be masked through a variety of techniques with a material that is preferably electrically and thermally insulating. This prevents the transmission of coagulation energy directly into the blood pool or collateral tissue, such as lung, esophagus and pericardial tissue, and directs the energy directly toward and into the tissue. For example, a layer of UV adhesive (or another adhesive) may be painted on preselected portions of the electrodes to insulate the portions of the electrodes not intended to contact tissue. Deposition techniques may also be implemented to position a conductive surface only on those portions of the assembly intended to contact tissue. Alternatively, a coating may be formed by dipping the electrodes in PTFE material or flexible non-electrically conducting material such as polyurethane.

Figure 13:
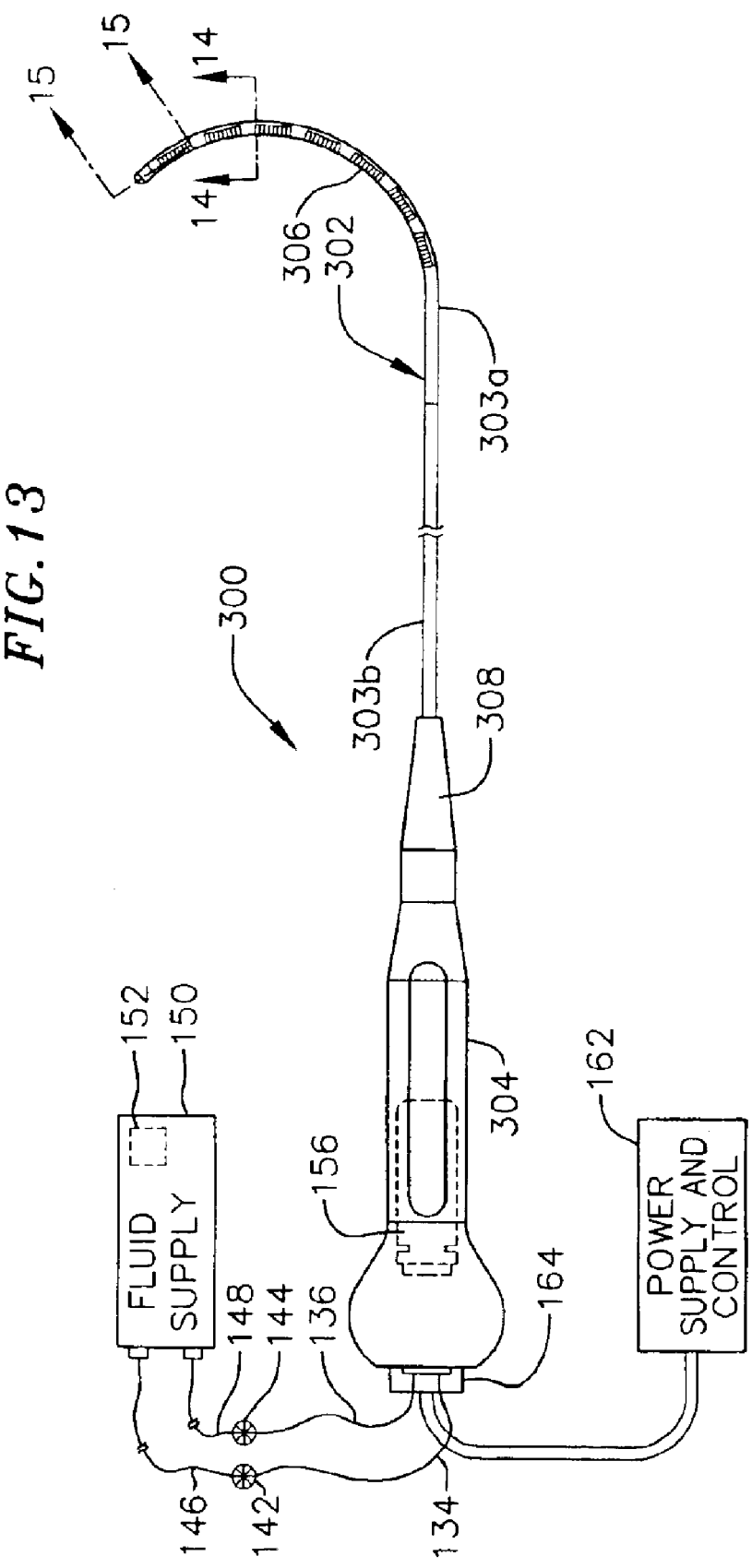
FIG. 13 is a plan view showing a surgical probe in accordance with a preferred embodiment of a present invention.
Figure 16:
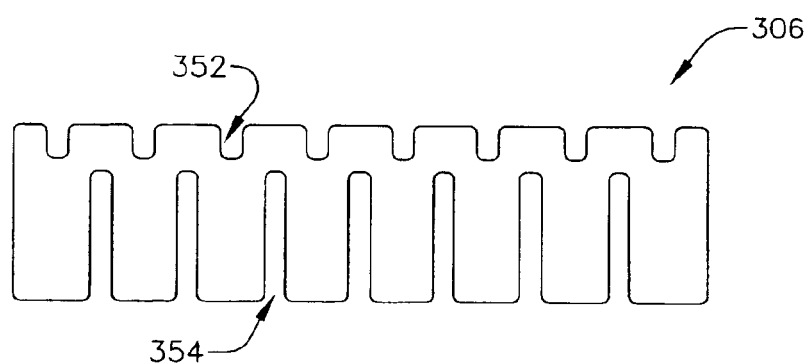
FIG. 16 is a side view of an electrode in accordance with a preferred embodiment of a present invention.

An alternative to masking is illustrated in FIGS. 13, 14 and 16. Like the exemplary probes 100 and 200, exemplary probe 300 includes seven spaced electrodes. Here, however, the electrodes 306 extend only partially around the outer structure 312. The electrodes 306 are preferably flexible and, to that end, include a plurality of slots 352 and 354 that are formed by laser cutting or stamping during manufacturing. The exemplary electrodes 306 are also provided with mounting flanges 356 that fit into slots (or "skives") 358 in the sides of the outer structure 312. Of course, each of the electrodes or other energy transmission devices described herein may be used in any embodiment of the present inventions and this includes, for example, use of the electrodes 306 on exemplary probes 100 and 200.

The exemplary flexible electrodes 106 and 306 are preferably about 4 mm to about 20 mm in length. In the preferred embodiments, the electrodes are 12.5 mm in length with 1 mm to 3 mm spacing, which will result in an energy transmission region that is about 1 cm to about 14 cm in length and the creation of continuous lesion patterns in tissue when coagulation energy is applied simultaneously to adjacent electrodes. For rigid electrodes, the length of the each electrode can vary from about 2 mm to about 10 mm. Using multiple rigid electrodes longer than about 10 mm each adversely effects the overall flexibility of the device, while electrodes having lengths of less than about 2 mm do not consistently form the desired continuous lesion patterns.

With respect to operation, the exemplary electrodes 106 and 306 may be operated in a uni-polar mode, in which the soft tissue coagulation energy emitted by the electrodes is returned through an indifferent patch electrode (not shown) externally attached to the skin of the patient. Alternatively, the electrodes may be operated in a bi-polar mode, in which energy emitted by one or more electrodes is returned through other electrodes. The amount of power required to coagulate tissue ranges from 5 to 150 w and depends on parameters such as set temperature and the flow rate of the fluid.

As illustrated for example in FIGS. 1–3 and 6, the electrodes 106 in the exemplary probe 100 are electrically coupled to individual power wires 154 that conduct coagulating energy to them. The power wires 154 are passed in conventional fashion through the lumen 120 (or 120') to a PC board 156 within the handle 104. Preferably, a plurality of temperature sensors 158 such as thermocouples or thermistors, may be located on, under, abutting the longitudinal end edges of, or in between, the electrodes 106. A reference thermocouple (not shown) may also be provided. The temperature sensors 158 are connected to the PC board 156 by signal wires 160 that pass though lumen 122 (or 120'). The PC board 156 is, in turn, connected to a power supply and control device 162 by a connector 164. Suitable temperature sensors and RF power supply and control devices are disclosed in U.S. Pat. Nos. 5,456,682, 5,582,609 and 5,755,715.

Similarly, the electrodes 106 in the exemplary probe 200 are electrically coupled to individual power wires 154 that pass through the lumen 220 to a PC board 156 within the handle 204 and the temperature sensors 158 are connected to the PC board by signal wires 160 that pass though the lumen 222. [Note FIGS. 8, 9 and 11.] The exemplary probe 300 includes a similar arrangement in that the electrodes 306 are electrically coupled to individual power wires 154 and the temperature sensors 158 are electrically coupled to individual signal wires 160. The power wires 154 and signal wires 160 are also connected to a PC board 156 in the handle 304. Here, however, the power wires 154 and signal wires 160 are located within the tubular member 313 that is itself located within the inlet lumen 316, as is noted above.

IV. Exemplary Methods

Surgical devices such as those illustrated above may be used to create transmural epicardial lesions to, for example, isolate the sources of focal (or ectopic) atrial fibrillation. Access to the heart may be obtained via a thoracotomy, thoracostomy or median sternotomy. Ports may also be provided for cameras and other instruments. With respect to lesions formed during open heart surgery, one exemplary lesion would extend from the incision used to gain access to the heart to the mitral valve annulus or some other anatomical barrier to reduce the potential for reentrant propagation around the incision. Lesions around the pulmonary veins may also be created. Exemplary non-cardiac uses include the treatment of tumors. Here, distal portion of the probe would be inserted into a tumor and then used to uniformly coagulate the entire tumor without charring.

An exemplary lesion formation procedure would proceed as follows. First, the energy emitting portion of a probe, such as one of the exemplary probes described above, will be placed in contract with the target tissue area. Preferably, the area will be relatively long (i.e. longer than a conventional tip electrode). The length of the area may, for example, range from about 1 cm to 14 cm depending on the length of the energy transmission region and portion thereof being utilized. Energy will then be transmitted to the tissue by the electrodes or energy transmission device(s) within the energy emitting portion as fluid flows through the lumens. The fluid will draw heat from the energy transmitting devices, thereby reducing their temperature. Energy transmission will preferably continue until the desired lesion is formed or until power is cutoff for energy control purposes.

Figure 17:
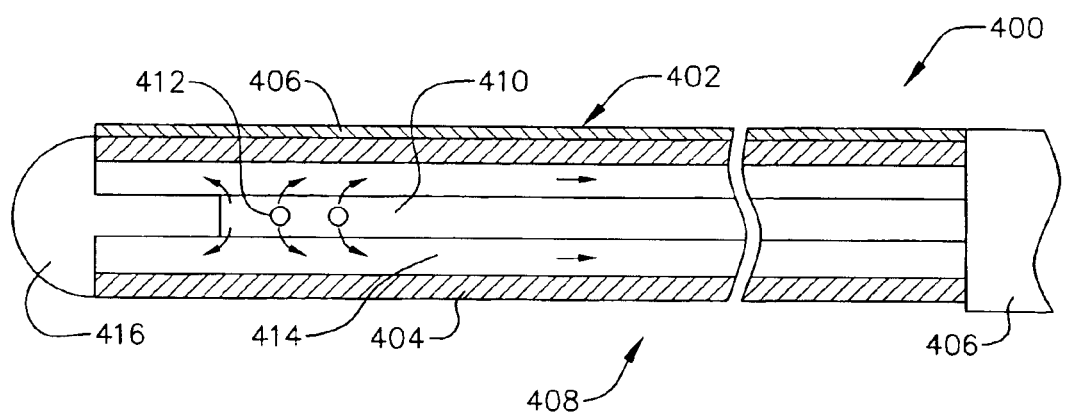
FIG. 17 is a side, partial section view of the distal portion of a probe in accordance with a preferred embodiment of a present invention.

Such a method may be performed with the surgical and catheter-based probes described above. However, it should be noted that practice of the method is not limited to the probes described above with reference to FIGS. 1–16. For example, as illustrated in FIG. 17, an exemplary surgical probe 400 in accordance with another invention herein includes a shaft 402 formed from a hypotube 404, which is preferably malleable and formed from energy transmitting material such as stainless steel, aluminum and platinum, that may be connected to an energy source. The proximal end is secured to a handle (not shown) similar to those described above. The proximal portion of the hypotube 404, which is about 2.0 inches to about 20.0 inches in length, and the area of the distal portion not intended to contact tissue are covered with electrically and thermally insulating material 406 such as Teflon or FEP, thereby forming an exposed elongate energy transmission region 408, which is about 0.1 inch to about 3.0 inches in length. Cooling fluid may be supplied to the inner surface of the hypotube 404 by way of a fluid inlet lumen 410 having apertures 412. Heat will be transferred from the hypotube 404 to the cooling fluid as the fluid flows through the outlet lumen 414 between the inlet lumen 410 and the inner surface of the hypotube. The exemplary probe 400 also preferably includes a soft tip 416 to prevent tissue trauma.

Although the present inventions have been described in terms of the preferred embodiments above, numerous modifications and/or additions to the above-described preferred embodiments would be readily apparent to one skilled in the art. Additionally, the scope of the inventions includes any combination of the elements from the various species and embodiments disclosed in the specification that are not already described. It is intended that the scope of the present inventions extend to all such modifications and/or additions and that the scope of the present inventions is limited solely by the claims set forth below.

I claim:

1. A soft tissue coagulation device, comprising:
    a shaft defining a distal end and including an outer structure formed from material that has a thermal conductivity of at least 0.8 W/m·K and is substantially electrically nonconductive;
    at least one energy transmission device supported on the outer structure in spaced relation to the distal end of the shaft; and
    at least one fluid lumen defined by the outer structure and located such that a portion thereof is aligned with the at least one energy transmission device.

2. A device as claimed in claim 1, wherein the shaft is relatively short.

3. A device as claimed in claim 1, wherein at least a portion of the shaft is relatively stiff.

4. A device as claimed in claim 3, wherein the shaft includes a malleable mandrel and the outer structure is mounted on the malleable mandrel.

5. A device as claimed in claim 3, wherein the shaft includes a tubular member defining a distal end and the outer structure extends distally from the distal end of the tubular member.

6. A device as claimed in claim 1, wherein the shaft include a proximal portion and a distal portion, the device further comprising:
    a steering apparatus that deflects the distal portion relative to the proximal portion.

7. A device as claimed in claim 1, wherein the shaft includes a pre-bent portion.

8. A device as claimed in claim 1, wherein the at least one fluid lumen comprises an inlet lumen and an outlet lumen.

9. A device as claimed in claim 8, wherein the inlet lumen and the outlet lumen define respective distal ends, the device further comprising:
    a non-conductive tip member defining a lumen that connects the distal ends of the inlet lumen and outlet lumen.

10. A device as claimed in claim 1, wherein the at least one fluid lumen includes inner and outer lumen surfaces defining a distance therebetween, the outer structure includes a wall defining a wall thickness between the at least one energy transmission device and the at least one fluid lumen, and the distance between the inner and outer lumen surfaces is greater than the wall thickness.

11. A device as claimed in claim 1, wherein the at least one energy transmission device comprises a plurality of longitudinally spaced energy transmission devices.

12. A device as claimed in claim 1, wherein the at least one energy transmission device comprises an electrode.

13. A soft tissue coagulation device, comprising:
    a shaft defining a distal end and a perimeter and including an outer structure formed from material that is relatively high in thermal conductivity and substantially electrically nonconductive;
    at least one energy transmission device supported on the outer structure in spaced relation to the distal end of the shaft and extending around less than the entire perimeter; and
    inlet and outlet lumens defined by the outer structure and located such that a portion of the inlet lumen is aligned with the at least one energy transmission device and is between a substantial portion of at least one the energy transmission device and the outlet lumen.

14. A device as claimed in claim 13, wherein the outlet lumen includes thermal insulation.

15. A soft tissue coagulation device, comprising:
    a shaft defining a proximal portion and a distal end and including an outer structure formed from material that is substantially electrically nonconductive;
    at least one energy transmission device supported on the outer structure in spaced relation to the distal end of the shaft;
    a fluid inlet lumen defined by the outer structure such that a wall having a wall thickness extends from the fluid inlet lumen to the at least one energy transmission device, located such that a portion thereof is aligned with the at least one energy transmission device, and including inner and outer lumen surfaces defining a distance therebetween that is greater than the wall thickness; and
    a fluid outlet lumen defined by the outer structure such that a wall having a wall thickness extends from the outlet inlet lumen to the at least one energy transmission device, located such that a portion thereof is aligned with the at least one energy transmission device, and including inner and outer lumen surfaces defining a distance therebetween that is greater than the wall thickness;

wherein the outer structure is configured such that the fluid inlet lumen includes an inlet associated with the proximal portion of the shaft, the fluid outlet lumen defines an outlet associated with the proximal portion of the shaft, the fluid outlet lumen is operably connected to the fluid inlet lumen and all fluid entering the outer structure though the fluid inlet will exit the outer structure through the fluid outlet.

16. A device as claimed in claim 15, wherein the shaft is relatively short.

17. A device as claimed in claim 15, wherein the shaft include a proximal portion and a distal portion, the device further comprising:
a steering apparatus that deflects the distal portion relative to the proximal portion.

18. A device as claimed in claim 15, wherein the inlet lumen and the outlet lumen define respective distal ends, the device further comprising:
a non-conductive tip member defining a lumen that connects the distal ends of the inlet lumen and outlet lumen.

19. A device as claimed in claim 15, wherein the at least one energy transmission device compnses an electrode.

20. A soft tissue coagulation device as claimed in claim 15, wherein the distance between the inner and outer lumen surfaces is at least two times greater than the wall thickness.

21. A soft tissue coagulation device, comprising:
a shaft defining a proximal portion and a distal end and including an outer structure formed from material that is substantially electrically nonconductive, at least a portion of the shaft being relatively stiff;
at least one energy transmission device supported on the outer structure in spaced relation to the distal end of the shaft;
a fluid inlet lumen defined by the outer structure such that a wall having a wall thickness is between the fluid inlet lumen and the at least one energy transmission device, located such that a portion thereof is aligned with the at least one energy transmission device, and including inner and outer lumen surfaces defining a distance therebetween that is greater than the wall thickness; and
a fluid outlet lumen defined by the outer structure and operably connected to the fluid inlet lumen;
wherein the outer structure is configured such that the fluid inlet lumen includes an inlet associated with the proximal portion of the shaft, the fluid outlet lumen defines an outlet associated with the proximal portion of the shaft, and all fluid entering the outer structure though the fluid inlet will exit the outer structure through the fluid outlet.

22. A soft tissue coagulation device, comprising:
a shaft defining a proximal portion and a distal end and including a malleable mandrel and an outer structure mounted on the malleable mandrel formed from material that is substantially electrically nonconductive;
at least one energy transmission device supported on the outer structure in spaced relation to the distal end of the shaft;
a fluid inlet lumen defined by the outer structure such that a wall having a wall thickness is between the fluid inlet lumen and the at least one energy transmission device, located such that a portion thereof is aligned with the at least one energy transmission device, and including inner and outer lumen surfaces defining a distance therebetween that is greater than the wall thickness; and a fluid outlet lumen defined by the outer structure and operably connected to the fluid inlet lumen;
wherein the outer structure is configured such that the fluid inlet lumen includes an inlet associated with the proximal portion of the shaft, the fluid outlet lumen defines an outlet associated with the proximal portion of the shaft, and all fluid entering the outer structure though the fluid inlet will exit the outer structure through the fluid outlet.

23. A soft tissue coagulation device, comprising:
a shaft defining a proximal portion and a distal end and including a tubular member defining a distal end and an outer structure extending distally from the distal end of the tubular member, the outer structure being formed from material that is substantially electrically nonconductive;
at least one energy transmission device supported on the outer structure in spaced relation to the distal end of the shaft;
a fluid inlet lumen defined by the outer structure such that a wall having a wall thickness is between the fluid inlet lumen and the at least one energy transmission device, located such that a portion thereof is aligned with the at least one energy transmission device, and including inner and outer lumen surfaces defining a distance therebetween that is greater than the wall thickness; and
a fluid outlet lumen defined by the outer structure and operably connected to the fluid inlet lumen;
wherein the outer structure is configured such that the fluid inlet lumen includes an inlet associated with the proximal portion of the shaft, the fluid outlet lumen defines an outlet associated with the proximal portion of the shaft, and all fluid entering the outer structure though the fluid inlet will exit the outer structure through the fluid outlet.

24. A soft tissue coagulation device, comprising:
a shaft defining a proximal portion and a distal end and including an outer structure formed from material that is substantially electrically nonconductive and a prebent portion;
at least one energy transmission device supported on the outer structure in spaced relation to the distal end of the shaft;
a fluid inlet lumen defined by the outer structure such that a wall having a wall thickness is between the fluid inlet lumen and the at least one energy transmission device, located such that a portion thereof is aligned with the at least one energy transmission device, and including inner and outer lumen surfaces defining a distance therebetween that is greater than the wall thickness; and
a fluid outlet lumen defined by the outer structure and operably connected to the fluid inlet lumen;
wherein the outer structure is configured such that the fluid inlet lumen includes an inlet associated with the pmximal portion of the shaft, the fluid outlet lumen defines an outlet associated with the proximal portion of the shaft, and all fluid entering the outer structure though the fluid inlet will exit the outer structure through the fluid outlet.

25. A soft tissue coagulation device, comprising:
a shaft defining a proximal portion and a distal end and including an outer structure formed from material that is substantially electrically nonconductive;
a plurality of longitudinally spaced energy transmission devices supported on the outer structure in spaced relation to the distal end of the shaft;

a fluid inlet lumen defined by the outer structure such that a wall having a wall thickness is between the fluid inlet lumen and the energy transmission devices, located such that a portion thereof is aligned with the energy transmission devices, and including inner and outer lumen surfaces defining a distance therebetween that is greater than the wall thickness; and a fluid outlet lumen defined by the outer structure and operably connected to the fluid inlet lumen;

wherein the outer structure is configured such that the fluid inlet lumen includes an inlet associated with the proximal portion of the shaft, the fluid outlet lumen defines an outlet associated with the proximal portion of the shaft, and all fluid entering the outer structure though the fluid inlet will exit the outer structure through the fluid outlet.

26. A soft tissue coagulation device, comprising:

a shaft defining a proximal portion, a distal end and a perimeter and including an outer structure formed from material that is substantially electrically nonconductive;

at least one energy transmission device supported on the outer structure in spaced relation to the distal end of the shaft and extending around less than the entire perimeter;

a fluid inlet lumen defined by the outer structure such that a wall having a wall thickness is between the fluid inlet lumen and the at least one energy transmission device, located such that a portion thereof is aligned with the at least one energy transmission device, and including inner and outer lumen surfaces defining a distance therebetween that is greater than the wall thickness; and a fluid outlet lumen defined by the outer structure and operably connected to the fluid inlet lumen;

wherein the outer structure is configured such that the fluid inlet lumen includes an inlet associated with the proximal portion of the shaft, the fluid outlet lumen defines an outlet associated with the proximal portion of the shaft, all fluid entering the outer structure though the fluid inlet will exit the outer structure through the fluid outlet, and the inlet lumen is between a substantial portion of at least one the energy transmission device and the outlet lumen.

27. A soft tissue coagulation device as claimed in claim 26, wherein the outlet lumen includes thermal insulation.

28. A soft tissue coagulation device, comprising:

a shaft defining a distal end and including a non-porous outer structure formed from material that is relatively high in thermal conductivity and substantially electrically nonconductive;

at least one energy transmission device supported on the outer structure in spaced relation to the distal end of the shaft; and at least one fluid lumen defined by the outer structure and located such that a portion thereof is aligned with the at least one energy transmission device.

29. A device as claimed claim 28, wherein the shaft is relatively short.

30. A device as claimed in claim 28, wherein at least a portion of the shaft is relatively stiff.

31. A device as claimed in claim 30, wherein the shaft includes a malleable mandrel and the outer structure is mounted on the malleable mandrel.

32. A device as claimed in claim 28, wherein the at least one fluid lumen comprises an inlet lumen and an outlet lumen.

33. A device as claimed in claim 28, wherein the at least one fluid lumen includes inner and outer lumen surfaces defining a distance therebetween, the outer structure includes a wall defining a wall thickness between the at least one energy transmission device and the at least one fluid lumen, and the distance between the inner and outer lumen surfaces is greater than the wall thickness.

34. A device as claimed in claim 28, wherein the at least one energy transmission device comprises a plurality of longitudinally spaced energy transmission devices.

35. A device as claimed in claim 28, wherein the at least one energy transmission device comprises an electrode.

36. A soft tissue coagulation device, comprising:

a shaft defining a distal end and including an outer structure formed from material that is relatively high in thermal conductivity and substantially electrically nonconductive;

at least one energy transmission device supported on the outer structure in spaced relation to the distal end of the shaft; and at least one fluid lumen defined by the outer structure and located such that a portion thereof is aligned with the at least one energy transmission device;

wherein the outer structure is configured such that the at least one energy transmission device will not come into contact with fluid that has passed through the at least one fluid lumen.

37. A device as claimed in claim 36, wherein the shaft is relatively short.

38. A device as claimed in claim 36, wherein at least a portion of the shaft is relatively stiff.

39. A device as claimed in claim 38, wherein the shaft includes a malleable mandrel and the outer structure is mounted on the malleable mandrel.

40. A device as claimed in claim 36, wherein the at least one fluid lumen comprises an inlet lumen and an outlet lumen.

41. A device as claimed in claim 36, wherein the at least one fluid lumen includes inner and outer lumen surfaces defining a distance therebetween, the outer structure includes a wall defining a wall thickness between the at least one energy transmission device and the at least one fluid lumen, and the distance between the inner and outer lumen surfaces is greater than the wall thickness.

42. A device as claimed in claim 36, wherein the at least one energy transmission device comprises a plurality of longitudinally spaced energy transmission devices.

43. A device as claimed in claim 36, wherein the at least one energy transmission device comprises an electrode.

44. A soft tissue coagulation device, comprising:

a shaft defining a proximal portion, a distal end and an exterior and including an outer structure formed from material that is substantially electrically nonconductive;

at least one energy transmission device located on the exterior of the outer structure in spaced relation to the distal end of the shaft;

a fluid inlet lumen defined by the outer structure such that a wall having a wall thickness is between the fluid inlet lumen and the at least one energy transmission device, located such that a portion thereof is aligned with the at least one energy transmission device, and including inner and outer lumen surfaces defining a distance therebetween that is greater than the wall thickness; and a fluid outlet lumen defined by the outer structure and operably connected to the fluid inlet lumen;

wherein the outer structure is configured such that the fluid inlet lumen includes an inlet associated with the proximal portion of the shaft, the fluid outlet lumen defines an outlet associated with the proximal portion of the shaft, and all fluid entering the outer structure though the fluid inlet will exit the outer structure through the fluid outlet.

45. A device as claimed in claim 44, wherein the shaft is relatively short.

46. A device as claimed in claim 44, wherein at least a portion of the shaft is relatively stiff.

47. A device as claimed in claim 46, wherein the shaft includes a malleable mandrel and the outer structure is mounted on the malleable mandrel.

48. A device as claimed in claim 44, wherein the at least one energy transmission device comprises a plurality of longitudinally spaced energy transmission devices.

49. A device as claimed in claim 44, wherein the at least one energy transmission device comprises an electrode.

50. A soft tissue coagulation device, comprising:

a shaft defining a proximal portion and a distal end and including an outer structure formed from material that is substantially electrically nonconductive;

at least one energy transmission device supported on the outer structure in spaced relation to the distal end of the shaft;

a fluid inlet lumen defined by the outer structure such that a wall having a wall thickness is between the fluid inlet lumen and the at least one energy transmission device, located such that a portion thereof is aligned with the at least one energy transmission device, and including inner and outer lumen surfaces defining a distance therebetween that is greater than the wall thickness; and a fluid outlet lumen operably connected to the fluid inlet lumen and defined by the outer structure such that a wall having a wall thickness is between the fluid outlet lumen and the at least one energy transmission device, located such that a portion thereof is aligned with the at least one energy transmission device, and includes inner and outer lumen surfaces defining a distance therebetween that is greater than the wall thickness;

wherein the outer structure is configured such that the fluid inlet lumen includes an inlet associated with the proximal portion of the shaft, the fluid outlet lumen defines an outlet associated with the proximal portion of the shaft, and all fluid entering the outer structure though the fluid inlet will exit the outer structure through the fluid outlet.

* * * * *